United States Patent [19]

DeWoskin

[11] 4,392,825
[45] Jul. 12, 1983

[54] STRAPPING

[75] Inventor: Irvin S. DeWoskin, St. Louis County, Mo.

[73] Assignee: Orthoband Company, Inc., Barnhart, Mo.

[21] Appl. No.: 323,673

[22] Filed: Nov. 23, 1981

[51] Int. Cl.³ ............................................. A61C 7/00
[52] U.S. Cl. ....................................................... 433/5
[58] Field of Search ................... 433/5; 24/31 V, 306

[56] References Cited

U.S. PATENT DOCUMENTS 3,765,093 10/1973 DeWoskin .............................. 433/5
3,866,276 2/1975 Perkins ................................... 24/306

Primary Examiner—Robert Peshock
Attorney, Agent, or Firm—Senniger, Powers, Leavitt and Roedel

[57] ABSTRACT

Strapping comprising first and second straps each having inner and outer faces, the straps being adapted to be placed in lapped face-to-face relation with the inner face of one strap engaging the outer face of the other strap. Fabric fastening material is provided on the engaging faces of the straps comprising a multiplicity of fastening elements projecting from one strap and a plush-like surface on the other interengageable with the fastening elements for securing the straps together. A loop on one of the straps at the lapped portion thereof releasably holds the straps together in face-to-face relation to maintain the fastening elements in interengagement with the plush-like surface. The fastening elements and plush-like surface are adapted to be separated for enabling relative longitudinal movement of the straps by inserting an elongate blade between the lapped portions of the straps.

27 Claims, 8 Drawing Figures

STRAPPING

BACKGROUND OF THE INVENTION

This invention relates to strapping, and more particularly to strapping of the type comprising a pair of straps which are adjustable lengthwise relative to one another and which may be releasably secured together in lapping relation by cooperable fastening means (e.g., fabric fastening material) on the engaging surfaces of the straps.

Reference may be made to my U.S. Pat. No. 3,765,093 showing orthodontic traction apparatus utilizing strapping of the above-mentioned type in conjunction with a pair of tension assemblies which are adapted to be stretched for applying posterior traction to the teeth via an orthodontic instrumentality (e.g., an arch wire) on the teeth in the patient's mouth. The strapping includes a neckband worn by the patient and a fastening strap attached to each tensioning assembly, the fastening straps being detachably securable to the neckband by means of fabric fastening material such as that commercially available under the trademark "Velcro". Traction is developed by pulling the fastening straps, when separated from the neckband, with a force equal to the desired traction to be applied, thereby stretching the tension members a corresponding distance. The traction is maintained by pressing the fabric fastening material of the fastening straps and the neckband together while the tension members are in stretched condition. Thereafter the straps are stapled to the neckband to prevent unintentional (or intentional but not prescribed) displacement of the straps relative to the neckband. While this arrangement has been entirely satisfactory for developing and maintaining the traction at the desired level, adjustment of the traction, as may be necessary during the course of a patient's treatment, requires (among other things) the removal of the staple and the application of a new staple.

SUMMARY OF THE INVENTION

Among the several objects of this invention may be noted the provision of improved strapping of the above-noted type wherein the straps are held secure in their adjusted position against tampering or accidental displacement relative to one another without the use of permanent fasteners (e.g., staples); the provision of such strapping in which the straps may be readily separated by inserting a specially designed tool between the lapped portions of the straps; the provision of such strapping in which the straps, when separated by the tool, may be readily moved to an infinite number of different positions (within a specified range) of relative adjustment, and may be secured together in adjusted position upon removal of the tool; and the provision of such strapping which is economical to manufacture.

Briefly, the strapping of this invention comprises first and second straps having inner and outer faces, the straps being adapted to be placed in lapped face-to-face relation with the inner face of one strap engaging the outer face of the other strap. Cooperable fastening means on the straps, comprising a multiplicity of fastening elements projecting from the engaging face of one strap and a plush-like surface on the engaging face of the other strap, secures the straps together when the fastening elements and plush-like surface are in interengagement. Loop means on one strap extending from one side of the strap to the other at the lapped portion thereof releasably holds the straps together in face-to-face relation thereby to maintain the fastening elements and plush-like surface in interengagement. The fastening elements and plush-like surface are adapted to be separated for enabling relative longitudinal movement of the straps by inserting an elongate blade between the lapped portions of the straps.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENTS

Figure 1:
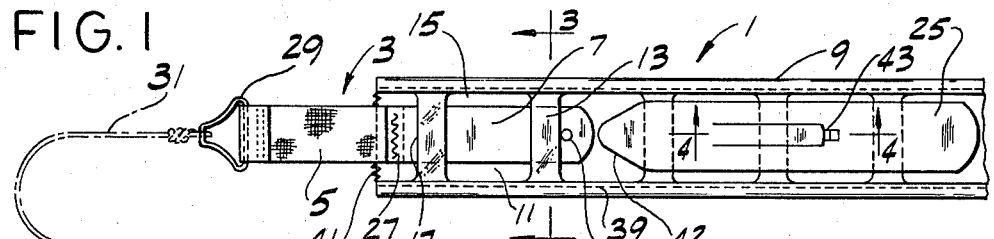
FIG. 1 is an elevation of a first embodiment of strapping of this invention comprising first and second straps, with a portion of the second strap being broken away and with a blade for separating the straps being shown adjacent an end of the first strap.
Figures 2, 3:
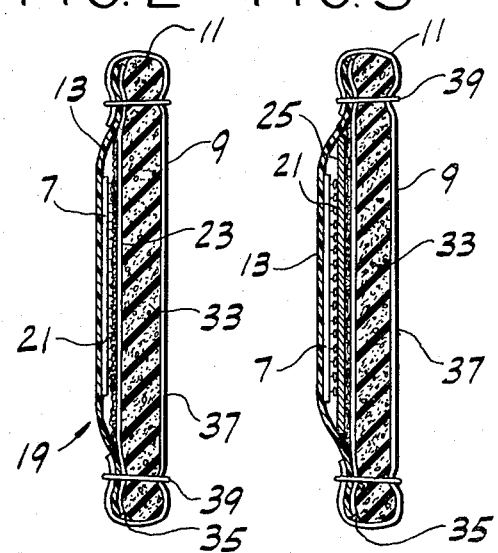
FIG. 2 is an enlarged section on line 2—2 of FIG. 1.
FIG. 3 is a section similar to FIG. 2 showing the blade inserted between the straps.

Referring to FIGS. 1–3, there is generally indicated at 1 a first embodiment of strapping of this invention adapted for use in extra-oral traction procedures, such as those described in my U.S. Pat. No. 3,765,093, for applying traction to a patient's teeth via an arch wire or other orthodontic instrumentality (not shown) on the teeth of the patient. The strapping 1, as used in these procedures, has a pair of tensioning means (one such means being generally indicated at 3), each tensioning means comprising a tension element 5 and a first strap 7 adapted to be pulled for developing a tension force in the tension element. The strapping further has a relatively long second strap 9 serving as a neckband to be worn around the patient's neck. The pull straps 7 are detachably secured adjacent opposite ends of the neck strap 9 for maintaining the tension force developed in the tension elements. The neck strap 9 is of generally uniform construction throughout its length, and the two tensioning means 3 are identical, so that the illustration and description of one end portion of the neck strap and the tensioning means associated therewith will suffice.

As illustrated in FIGS. 1 and 2, the neck strap 9 comprises an inner strip 11 having an outer face, (i.e., the face toward the viewer as shown in FIG. 1) engageable by an inner face of the pull strap 7 (i.e., the face away from the viewer as shown in FIG. 1) when the straps are in lapping relation. The neck strap 9 also includes an outer strip 13 having a series of openings 15 therein forming loops 17 extending from one side of the neck strap to the other on the outside of the inner strip 11. The openings 15 are of greater width than the pull strap 7 thereby enabling the latter to be inserted between the loops and the inner strip 11 of the neck strap. Indicated generally at 19 on the straps 7, 9 is cooperable fastening means comprising a multiplicity of fastening elements 21 projecting from the inner face of the pull strap and a plush-like surface 23 on the outer face of inner strip 11 of the neck strap, the fastening elements and plush-like surface being adapted to secure the straps 7, 9 together when in interengagement. As described more fully hereinafter, the fastening elements and plush-like surface are adapted to be held apart by an elongate blade 25 inserted between the engageable faces of the straps 7, 9 to enable insertion of the pull strap between the loops 17 and the inner strip 11 of the neck strap. Upon removal of the blade, the fastening elements 21 and plush-like surface 23 are adapted to be pressed into interengagement for securing the straps together, with the loops 17 extending over the pull strap 7 to releasably hold the straps together in face-to-face relation thereby to maintain the interengagement of the elements 21 and surface 23.

The tension element 5 comprises an elastic band of fabric strip material capable of developing tension force upon being stretched. As illustrated in FIG. 1, the band 5 projects forward (i.e., toward the left) beyond the end of the neck strap and is attached at its rearward end, as by stitching 27, to the forward end of the pull strap 7, and is looped at its forward end through a closed hook 29 and folded back and stitched to itself. The closed hook 29 is attached to a face bow 31 which is adapted to be attached to the orthodontic instrumentality (not shown) on the patient's teeth. The pull strap 7 is formed from a piece of suitable fabric fastening material having a multiplicity of the stated fastening elements 21 projecting from the inner face thereof. The fastening elements are preferably of the mushroom-head type, which exhibit relatively high holding power.

The outer strip 13 of the neck strap is formed from a continuous length of suitable flexible sheet material such as polyurethane, polyester or polyolefin film or polyester fabric. The openings 15 are cut in the sheet material at equal intervals along its length, the openings being of generally square shape and extending from adjacent one side edge of the neck strap to the other. The inner strip 11 of the neck strap is a composite strip comprising a central layer 33 of flexible compressible pad material (e.g., polyester or polyurethane foam) of relatively heavy loft for providing a cushioning effect, a first or outer facing layer 35 formed from a second piece of fabric fastening material presenting at its exposed face the stated plush-like surface 23, and a second or inner facing layer 37 of suitable flexible sheet material. The inner facing layer 37 is of a width greater than the central and outer facing layers 33, 35 and the outer strip 13, and has side margins folded around the side edges of these layers and overlying the side margins of the outer strip 13. The inner and outer strips 11, 13 of the neck strap are seamed together, as by lines of stitching 39, along their side edge margins. The loops 17 are thus free of attachment to the central portion of the inner strip 11, thereby enabling the pull strap 7 to be received therebetween. The ends of the neck strap are finished by overstitching 41.

Figure 4:
FIG. 4 is a section on line 4—4 of FIG. 1.

Being formed of fabric fastening material, the cooperable fastening means 19 provides a connection between the straps 7, 9 which strongly resists separation under tensile forces acting on the straps generally in the plane of the lapped portions of the straps, but which provides little resistance to forces acting generally perpendicular to the plane of the lapped portions. Thus the cooperable fastening means is especially suitable both for securing the pull straps to the neck strap for maintaining the traction force developed by the tensioning means 3, and for enabling the blade 25 readily to be inserted between the straps to separate them by moving the straps outwardly away from one another. The blade is formed from a blank of suitable relatively rigid sheet material such as thin gauge sheet metal to have a greater length and width than the pull strap thereby enabling it to hold the pull strap 7 from the inner strip 11 of the neck strap along the entire length of the pull strap. An end 42 of the blade is tapered to facilitate the insertion of the blade between the fastening elements 21 and the plush-like surface 23 to separate the straps. As shown best in FIGS. 1 and 4, the blade 25 has a struck-out portion formed into a finger 43 projecting at right angles to one face of the blade. This finger is receivable in an opening 44 in the pull strap 7 and constitutes means for moving the pull strap relative to the neck strap once the blade is inserted therebetween to disengage the fastening elements 21 from surface 23. In this connection, it will be noted that the distance between the tapered end of the blade and the finger is greater than the distance between the opening 44 and the end of the pull strap attached to the elastic band 5.

In the use of the FIG. 1 strapping for extra-oral traction procedures, the neck strap 9 is placed around the back of the patient's neck and each tensioning means 3, with its elastic band 5 in stretched condition, is connected to the neck strap and to the orthodontic instrumentality (not shown) via the face bow 31 for applying traction to the teeth. The connection of each tensioning means 3 to the neck strap 9 is effected by inserting the blade 25 between the loops 17 and the inner strip 11 at the respective end of the neck strap, inserting the pull strap 7 between the loops and the blade, pulling the pull strap to develop the desired traction, withdrawing the blade and pressing the fastening elements 21 and plush-like surface 23 into interengagement to secure the straps 7, 9 together to maintain the desired traction forces. The fact that the loops 17 overlie the pull strap 7 is advantageous in that this renders the pull strap generally inaccessible to tampering by the patient or accidental displacement relative to the neck strap 9. Adjustment of the traction may be effected by inserting the blade 25 between the engaging faces of the pull strap 7 and inner strip 11 of the neck strap, moving the pull strap longitudinally relative to the inner strip 11, removing the blade, and pressing the fastening elements 21 and plush-like surface 23 back into interengagement. The use of fabric fastening material to detachably secure the tensioning means 3 to the neck strap permits the tensioning means to be fastened at any position along the neck strap thereby to provide for infinite adjustment of the traction force applied to the teeth.

While the strapping 1 has been shown in the drawings and described above as having its cooperative fastening means 19 so arranged that the fastening elements 21 are on the pull strap and the plush-like surface 23 is on the inner strip of the neck strap, it is contemplated that this arrangement could be reversed. Moreover, while the fastening elements 21 are shown and described as being of mushroom-head type and the tension element 5 as being an elastic band, it is contemplated that the fastening elements may have other configurations, such as a hook shape, for example, and the tension element may be of other known constructions, such as the spring tension element disclosed in my U.S. Pat. No. 3,765,093.

Figure 5:
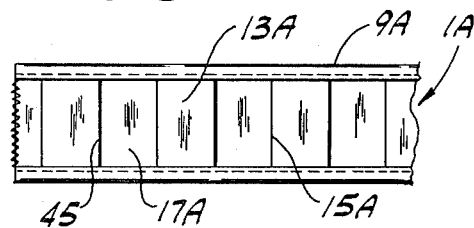
FIG. 5 is an elevation of a second embodiment of strapping of this invention, with a first strap being removed and a portion of a second strap broken away.

FIG. 5 illustrates a second embodiment of the strapping of this invention generally indicated at 1A which is similar to the first embodiment except that the outer strip 13A of the neck strap 9A has slits 45 therein constituting the stated openings 15A and the loops 17A thus cover the entire outer face of the inner strip of the neck strap.

Figure 6:
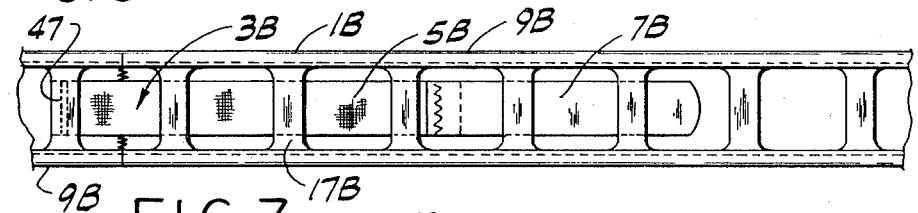
FIG. 6 is an elevation of a third embodiment of strapping of this invention as formed into a loop, portions of the strapping being broken away.

FIG. 6 illustrates a third embodiment of strapping of this invention generally indicated at 1B which is similar to the first embodiment except that the second strap 9B (comparable to neck strap 9) is longer and the tensioning means 3B is attached, as by stitching 47, at one end to an end of the second strap and is adapted to be detachably secured at its other end to the other end of the second strap. This strapping 1B is thus well suited for use as a belt, such as a restraining belt. In this regard, FIG. 6 shows the strapping 1B arranged in a loop, with the ends of the second strap 9B in lapping relation with each other and with the pull strap 7B of and tensioning means 3B secured to the second strap.

Figure 7:
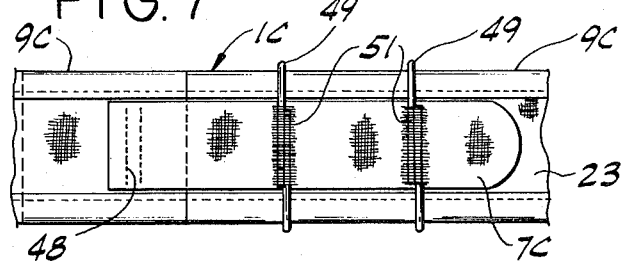
FIG. 7 is an elevation of a fourth embodiment of strapping of this invention as formed into a loop, portions of the strapping being broken away.
Figure 8:
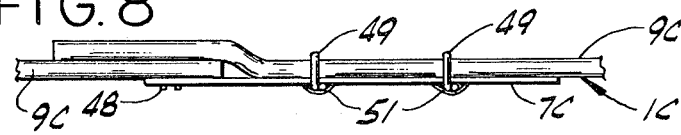
FIG. 8 is a top plan of FIG. 7.

FIGS. 7 and 8 illustrate a fourth embodiment of strapping of this invention generally indicated at 1C which is similar to the third embodiment except that the pull strap 7C is secured, as by stitching 48, to the second strap 9C, and the second strap does not have an outer strip for holding the fastening elements and plush-like surface 23 in interengagement but, rather, includes a pair of wire loops 49 for holding the lapped portions of the straps together. While the loops 49 are shown as being secured, as by stitching 51, to the pull strap 7C and as being of closed configuration for extending completely around both straps, it is contemplated that the loops may be secured to the second strap 9C and may be of an open configuration thereby extending only partially around the lapped portions of the straps.

It will be observed that each of the four embodiments 1–1C of the strapping comprises first and second straps 7–7C, 9–9C each having inner and outer faces, the straps being adapted to be placed in lapped face-to-face relation with the inner face of one strap engaging the outer face of the other strap, cooperable fastening means 19 comprising a multiplicity of fastening elements 21 projecting from the engaging face of one strap and a plush-like surface 23 on the engaging face of the other strap for interengagement with the fastening elements thereby to secure the straps together, and loop means (e.g., loops 17–17B and 49) on one of the straps at the lapped portion thereof for releasably holding the straps together in face-to-face relation thereby to maintain the interengagement against tampering, accidental dislodgement, etc. It will be further observed that in each embodiment, the fastening elements and plush-like surface are adapted to be separated for enabling relative longitudinal movement of the straps by inserting an elongate blade 25 between the lapped portions of the straps.

In view of the above, it will be seen that the several objects of the invention are achieved and other advantageous results attained.

As various changes could be made in the above constructions without departinng from the scope of the invention, it is intended that all matter contained in the above description or shown in the accompanying drawings shall be interpreted as illustrative and not in a limiting sense.

What is claimed is:

1. Strapping having:
    tensioning means comprising a first strap adapted to be pulled for developing a tension force;
    a second substantially nonstretchable strap including an inner strip and an outer strip on one face constituting the outside face of the inner strip, said outer strip having openings therein spaced at intervals longitudinally of the strip and extending between the side edges of the strip; and
    cooperable fastening means on the first strap and on the outside face of the inner strip of the second strap,
    said first strap being adapted to be inserted between the inner and outer strips of the second strap and pulled to develop the desired tension force, said cooperable fastening means comprising a multiplicity of fastening elements projecting from either the first strap or the inner strip of the second strap, the other having a plush-like surface for interengagement with said fastening elements thereby to secure the first and second straps together with said tensioning means applying said tension force,
    said fastening elements and plush-like surface being adapted to be held apart as the first strap is inserted between the inner and outer strips of the second strap by an elongate blade inserted between the first strap and the inner strip of the second strap, said blade being removable to permit interengagement of said fastening elements and said plush-like surface for securing the first and second straps together, the outer strip of the second strap at least partially covering the first strap to ensure that said interengagement is maintained.

2. Strapping as set forth in claim 1 wherein the outer face of the inner strip of the second strap presents said plush-like surface, and the fastening elements project from the inner face of the first strap.

3. Strapping as set forth in claim 1 in combination with an elongate blade of relatively rigid sheet material adapted for insertion between the first strap and the inner strip of the second strap for holding apart said fastening elements and said plush-like surface.

4. Strapping as set forth in claim 3 wherein said blade is of greater length and width than said first strap.

5. Strapping as set forth in claim 3 wherein said blade has a tapered end thereby to facilitate insertion of the blade between the first strap and the inner strip of the second strap.

6. Strapping as set forth in claim 3 wherein said blade has means thereon engageable with said first strap for moving it relative to the second strap when the blade is inserted between the first strap and the inner strip of the second strap.

7. Strapping as set forth in claim 6 wherein said means on the blade comprises a finger projecting from one face of the blade receivable in an opening in the first strap.

8. Strapping as set forth in claim 3 wherein the openings in the outer strip of the second strap are wider than the blade for enabling the blade to be inserted between the inner and outer strips of the second strap.

9. Strapping as set forth in claim 8 wherein the outer strip of the second strap is formed from a continuous length of flexible sheet material having slits therein spaced at intervals longitudinally of the strip, said slits constituting said openings in the outer strip.

10. Strapping as set forth in claim 8 wherein the outer strip of the second strap is formed from a continuous length of flexible sheet material having said openings cut therein.

11. Strapping as set forth in claim 1 wherein the inner and outer strips of the second strap are seamed together along their side edge margins.

12. Strapping as set forth in claim 1 wherein said inner strip of said second strap is a composite strip comprising a central layer of flexible compressible pad material of relatively heavy loft for providing a cushioning effect, a first flexible facing layer on the outside face of the central layer, and a second flexible facing layer on the inside face of the central layer, the outer face of said first facing layer presenting said plush-like surface.

13. Strapping as set forth in claim 12 wherein said second facing layer has a width greater than that of the central and first facing layers and said outer strip and has side margins folded around the side edges of the central and first facing layers and overlying the side margins of said outer strip.

14. Strapping as set forth in claim 1 wherein the tensioning means further comprises a tension element adapted to develop tension force upon being stretched, said tension element being attached at one end thereof to an end of said first strap and extending beyond an end of the second strap when the first strap is secured to the second strap, said tension element being adapted to apply tension force to an instrumentality attached to the other end of the tension element when the tension element is held in stretched condition between the first strap and the instrumentality.

15. Strapping as set forth in claim 1 wherein the tension element is of elastic strip material.

16. Strapping comprising:
first and second straps each having inner and outer faces, said straps being adapted to be placed in lapped face-to-face relation with the inner face of one strap engaging the outer face of the other strap;
cooperable fastening means on the straps comprising a multiplicity of fastening elements projecting from the engaging face of one strap and a plush-like surface on the engaging face of the other strap for interengagemennt with said fastening elements thereby to secure the straps together; and
loop means secured to one strap and extending from one side of the strap to the other at the lapped portion thereof for releasably holding the straps together in face-to-face relation thereby to maintain said interengagement; and
an elongate blade of relatively rigid sheet material adapted for insertion between the lapped portions of the first and second straps for holding apart said fastening elements and plush-like surface thereby to enable relative longitudinal movement of the straps.

17. Strapping as set forth in claim 16 wherein the loop means is of a closed shape and extends around both straps at the lapped portions thereof.

18. Strapping as set forth in claim 17 wherein the loop means comprises a closed loop of wire secured to one of the straps.

19. Strapping as set forth in claim 16 wherein the fastening elements project from the inner face of the first strap, the outer face of the second strap presenting said plush-like surface.

20. Strapping as set forth in claim 19 wherein the first strap is attached to one end of the second strap and overlaps the second strap when the strapping is formed into a loop.

21. Strapping as set forth in claim 19 wherein said second strap comprises a composite strip comprising a central layer of flexible compressible pad material of relatively heavy loft for providing a cushioning effect, a first flexible facing layer on the outside face of the central layer, and a second flexible facing layer on the inside face of the central layer, the outer face of said first facing layer presenting said plush-like surface.

22. Strapping as set forth in claim 21 wherein said second facing layer has a width greater than that of the central and first facing layers and has side margins folded around the side edges of the central and first facing layers.

23. Strapping as set forth in claim 19 wherein the second strap further comprises a second strip having openings therein spaced at intervals longitudinally thereof and extending between the side edges thereof, the second strip extending over the outer face of said composite strip and constituting said loop means, the strips being joined along their side edge margins.

24. Strapping as set forth in claim 16 wherein said blade is of greater length and width than said first strap.

25. Strapping as set forth in claim 24 wherein said blade has a tapered end thereby to facilitate insertion of the blade between the lapped portions of the straps.

26. Strapping as set forth in claim 16 wherein said blade has means thereon engageable with one strap for moving it relative to the other strap when the blade is inserted between the lapped portions of the straps.

27. Strapping as set forth in claim 26 wherein said means on the blade comprises a finger projecting from one face of the blade receivable in an opening in said one strap.

* * * * *